(12) United States Patent
Montagnino

(10) Patent No.: US 6,472,617 B1
(45) Date of Patent: Oct. 29, 2002

(54) BODY FAT SCALE WITH HAND GRIPS

(75) Inventor: James Montagnino, St. Charles, IL (US)

(73) Assignee: Sunbeam Products, Inc., Boca Raton, FL (US)

( * ) Notice: Subject to any disclaimer, the term of this patent is extended or adjusted under 35 U.S.C. 154(b) by 0 days.

(21) Appl. No.: 09/684,049

(22) Filed: Oct. 6, 2000

(51) Int. Cl.[7] .................. G01G 21/00; G01G 21/28; A61B 5/05

(52) U.S. Cl. .................. 177/126; 177/238; 177/245; 600/547

(58) Field of Search .................. 600/547; 177/126, 177/127, 238, 239, 240, 241, 242, 243, 244, 245

(56) References Cited

U.S. PATENT DOCUMENTS

| | | | | |
|---|---|---|---|---|
| 3,984,645 A | * | 10/1976 | Kresch | 379/340 |
| 4,114,736 A | * | 9/1978 | Scherenberg | 191/12.4 |
| 4,441,568 A | * | 4/1984 | Heffner | 177/129 |
| 4,499,341 A | * | 2/1985 | Boyd | 191/12.4 |
| 5,074,863 A | * | 12/1991 | Dines | 606/41 |
| 5,410,597 A | * | 4/1995 | Kepley, III et al. | 379/449 |
| 5,579,782 A | * | 12/1996 | Masuo | 600/547 |
| 5,669,571 A | * | 9/1997 | Graybill | 242/378.1 |
| 6,002,937 A | * | 12/1999 | Young et al. | 455/462 |
| 6,088,615 A | * | 7/2000 | Masuo | 600/547 |
| 6,280,396 B1 | * | 8/2001 | Clark | 600/547 |
| 6,308,096 B1 | * | 10/2001 | Masuo | 600/547 |
| 6,327,494 B1 | * | 12/2001 | Sakai | 600/547 |
| 6,369,337 B1 | * | 4/2002 | Machiyama et al. | 177/25.13 |

\* cited by examiner

Primary Examiner—Randy W. Gibson
(74) Attorney, Agent, or Firm—Kramer, Levin, Naftalis & Frankel, LLP

(57) ABSTRACT

A practical and accurate body fat scale which utilizes handheld body fat sensors connected to the scale base to aid in determining body fat content. The handheld sensors detect the higher concentrations of fat located in the upper body, as compared to the lower extremities, and therefore provides an accurate and meaningful assessment of body fat content.

14 Claims, 3 Drawing Sheets

BODY FAT SCALE WITH HAND GRIPS

FIELD OF INVENTION

The present invention relates to a method and apparatus for accurately measuring body fat.

BACKGROUND INFORMATION

A measurement of the amount of fat in a person's body can be valuable and useful for several reasons. First, fat measurements can be a valuable aid in monitoring body tone. Further, such measurements provide a means for monitoring and indicating the progress of a fitness program. An indication of a quantitative progression can be psychologically valuable as a means of encouraging continued participation. In addition, when a person embarks on a fitness program, he or she will often gain weight by virtue of added muscle mass. Thus, based solely on weight gain or loss as measured by conventional scales, the person may erroneously believe he or she is becoming "fatter", when in fact the ratio of fat to lean body tissue is actually declining. Accurate measurements of the ratio of fat to lean tissue will correct this misinformation.

Customary methods for measuring the ratio of fat to lean tissue include hydrostatic body weighing. This method is used to estimate body fat by calculating body density from the measured weight value under water as a method for accurately measuring body fat in vivo. This underwater body weighing method, however, requires a large facility, and necessitates skillful measuring techniques. In addition, this method is inconvenient for the person whose body fat is being measured.

Another presently accepted method of determining actual body fat percentage comprises skin fold measurements. Calipers are used to measure the thickness of a fold of skin in various areas of the body. Equations have been developed which can translate this measurement into a logarithmic value which then can be translated into a percent designation of body weight which comprises body fat. However, the skin fold technique, while accurate, requires the use of expensive calipers which require technical skill in their use.

Another accepted method for measuring body fat content is the use of handheld devices. Several commercially available handheld body fat monitors are presently available. A major drawback in the use of such monitors is that the user must separately enter data, such as weight, to obtain an accurate measurement of body fat percentage. Accordingly, compliance with a fitness program which monitors body fat percentage is compromised.

Still another accepted method of determining body fat content utilizes scales which comprise body fat sensors that measure the impedance through an individual's legs. The measured impedance can be translated into a body fat percentage. However, the distribution of body fat is not uniform, in particular with respect to the lower extremities. Many people have significantly lower body fat measurements for the lower extremities as compared to the upper body or the body as a whole. Thus, such body fat sensors do not provide reliable readings and routinely underestimate actual body fat percentages.

Accordingly, there exists a need for a body fat measuring device that is both accurate and easy to use.

SUMMARY OF THE INVENTION

The present invention provides a practical and accurate body fat scale which utilizes handheld body fat sensors which are connected to the scale base to aid in determining body fat content. These handheld sensors detect the higher concentrations of fat located in the upper body, as compared to the lower extremities, and therefore provide a more accurate and meaningful assessment of body fat content.

According to an exemplary embodiment of the present invention, there is provided a body fat scale which comprises a handheld body fat sensor connected to a scale platform. The body fat scale provides simultaneous measurements of the user's weight and of the impedance between extremities of the user's body. These measurements may be used to calculate the user's percentage body fat.

In an exemplary embodiment, the handheld body fat sensors are connected to the scale by retractable cables. In another exemplary embodiment, the body fat scale comprises a pedestal style display and the handheld sensors are attached to the upper portion of the pedestal. In still another embodiment of the present invention, the handheld body fat sensors are connected to the base with retractable, telescoping connectors.

According to another aspect of the present invention, there is provided a method for measuring body fat by the steps of measuring impedance between extremities of a body utilizing a hand held body fat sensor, and calculating body fat from numeric values of physical conditions such as the measured body impedance value, weight, and gender.

The present invention will now be described in further detail with respect to exemplary embodiments as illustrated in the accompanying Figures.

DETAILED DESCRIPTION

In general, body fat percentage is an index which measures the amount of fat in an individual as a function of that individual's total weight. When this percentage exceeds certain levels, body fat may contribute to various health disorders. Accordingly, devices which can accurately and conveniently measure a person's body fat are useful tools to evaluate the present status of an individual and to monitor the progression of a fitness program. Fat does not conduct electrical current as readily as non-fat tissue such as muscle. Therefore, body fat sensors are used to measure the conductivity of weak current passed through the body. The higher the body fat content through which the current passes, the greater the measured impedance. Thus, impedance readings can be used to calculate body fat percentage.

Figure 1A:
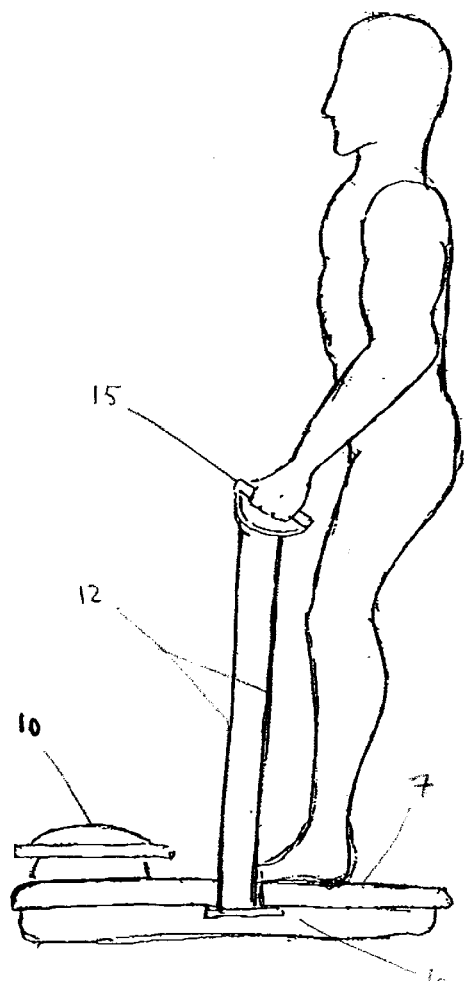
FIG. 1A is a side view of an exemplary embodiment of a body fat scale in which the handheld sensors are connected to the scale with a retractable cable connection.
Figure 1B:
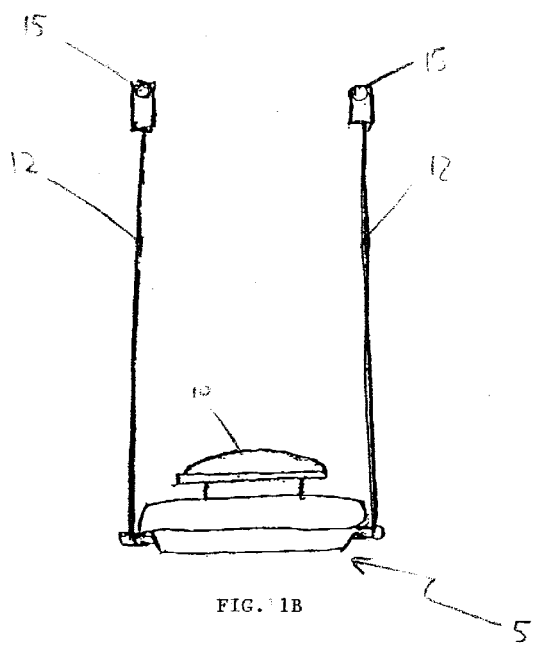
FIG. 1B is a front view of the body fat scale of FIG. 1A showing the handheld sensors in the extended position.
Figure 1C:
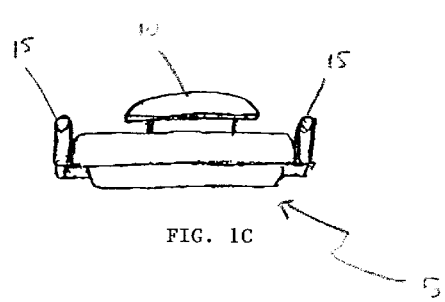
FIG. 1C is a front view of the body fat scale of FIG. 1A showing the handheld sensors in the retracted position.

FIGS. 1A–C illustrate an exemplary embodiment of a body fat scale in accordance with the present invention. This apparatus comprises a base 5 having a platform 7 and a monitor 10 on the upper surface of the base 5. A pair of retractable cables 12, each having a proximal end and a distal end, extends from the lateral aspects 6 of the base 5. The proximal end of the cables may be attached to a spring retraction system, while the distal end of the cables are connected to a handheld body fat sensor 15.

Figure 2A:
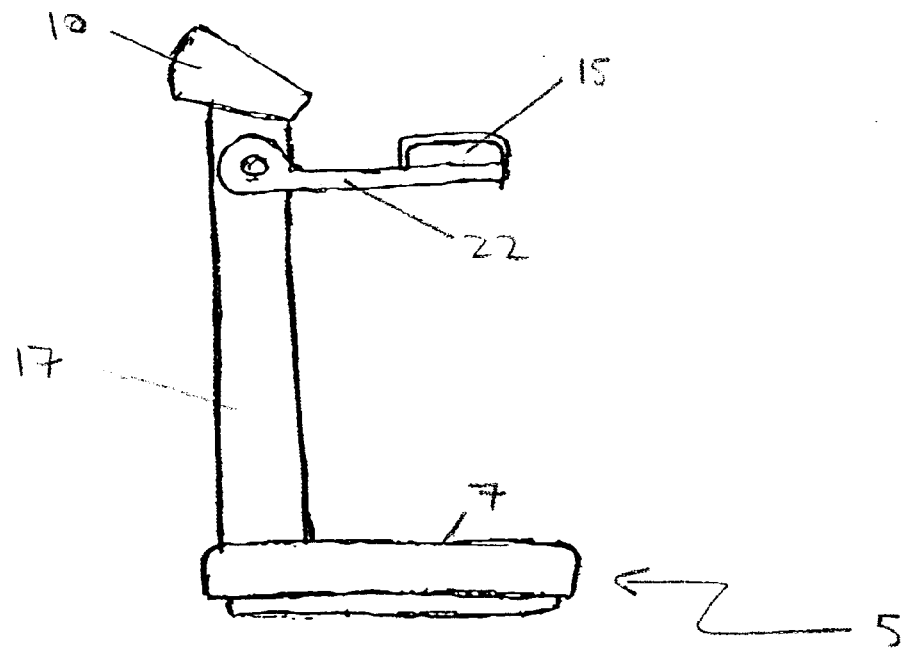
FIG. 2A is a side view of an exemplary embodiment of a body fat scale in which the handheld sensors are in an extended position and are connected to a pedestal style display.
Figure 2B:
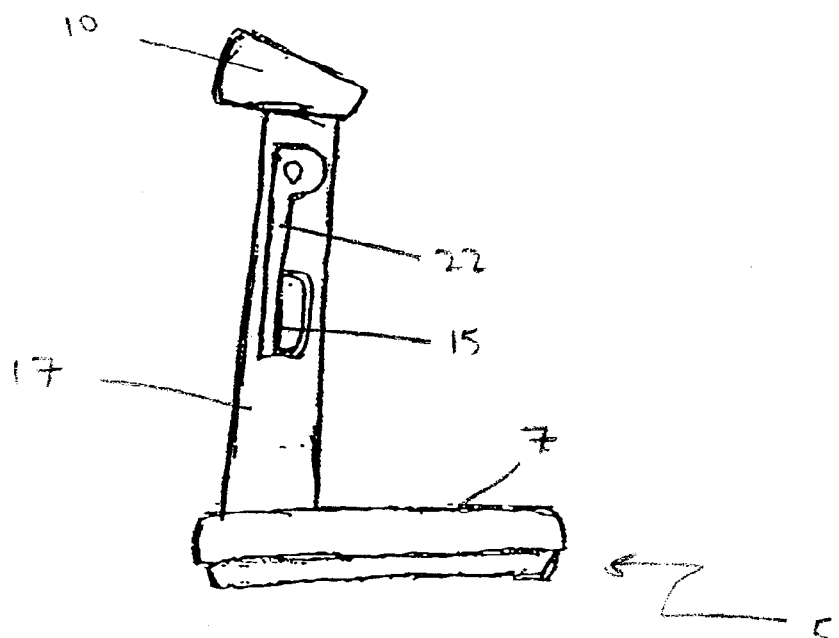
FIG. 2B is the body fat scale of FIG. 2A in which the handheld sensors are in the retracted position.

As shown in FIGS. 2A and 2B in another embodiment of the present invention a body fat scale may comprise a pedestal 17 which extends between the base 5 and the monitor 10. The pedestal 17 has a proximal end attached to the base 5 and a distal end attached to the monitor 10. The pedestal 17 extends in an approximately vertical manner from the base 5. The handheld body fat sensor 15 may be connected to pedestal 17 with retractable lever arms 22 which extend from each side of the pedestal 17. The retractable lever arms 22 may be attached near the distal end of the pedestal 17. In the extended position, illustrated by FIG. 2A, the retractable lever arms 22 may form approximately perpendicular angles with the pedestal 17. In the retracted position, illustrated by FIG. 2B, the retractable lever arms 22 may be folded against the sides of the pedestal 17.

Figure 3A:
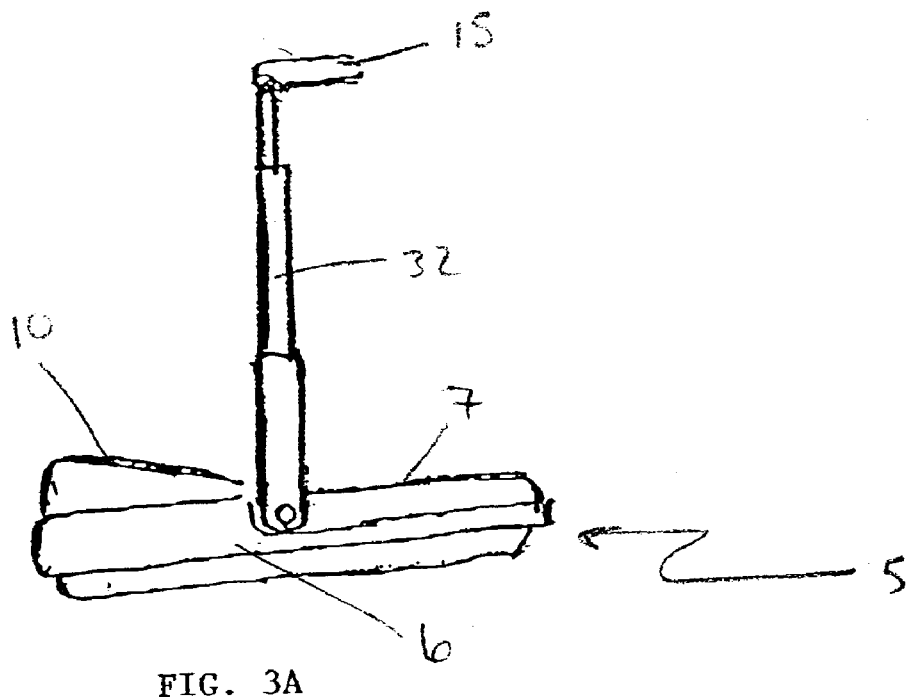
FIG. 3A is a side view of an exemplary embodiment of a body fat scale in which the handheld sensors are in an extended position and are connected to the scale base via a telescoping connector.
Figure 3B:
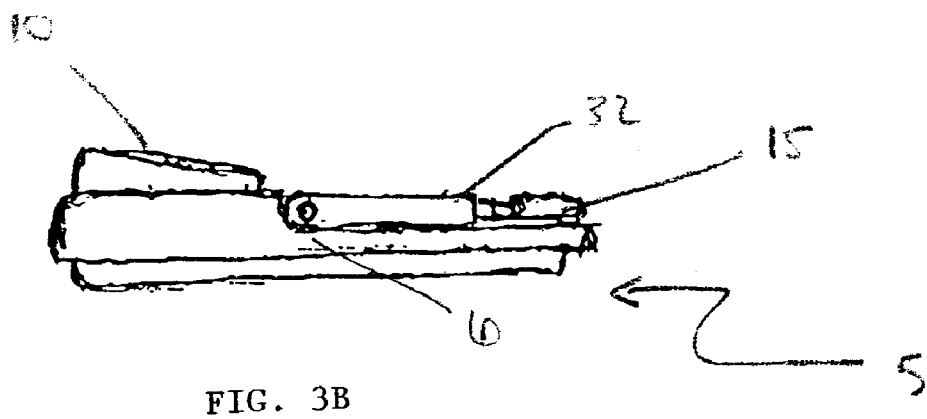
FIG. 3B is the body fat scale of FIG. 3A in which the hand held sensors are in the retracted position.

FIGS. 3A and 3B illustrate another exemplary embodiment of the present invention. As shown in FIGS. 3A and 3B the body fat scale may comprise a pair of retractable telescoping extensions 32, each having a proximal end and a distal end. The proximal end may extend from the lateral aspect 6 of the base 5, while the distal end may connect to the handheld body fat sensors 15.

In the extended position, the retractable telescoping extensions 32 may extend in an approximately vertical manner. In the retracted position, the retractable telescoping extensions 32 may be retracted and folded next to the lateral edges of the base 5.

The base 5 may be comprised of a variety of materials, including but not limited to sheet metal, plastic or glass. The platform 7 portion of the base 5 may be covered by a mat which gives the platform 7 a softer feel. The mat may be, for example, a thin vinyl layer.

The podium 17 also may be comprised of a variety of materials, including but not limited to metal, injection molded plastic, or aluminum extrusion material. Telescoping extensions 32 may comprise, for example, metal tubing or plastic tubing.

In an exemplary embodiment, retractable cables 12 are connected to the handheld body fat sensor 15 and are retractable, for example, via a negator type spring assembly. Other means of retraction include, but are not limited to motorized spring systems and counter-balance weight systems. The retractable cables 12 may comprise an external sheath which surrounds a wire cord capable of conducting the current used in impedance measurements. The external sheath may comprise, for example, "bungy cord" material. Alternatively, a flat synthetic cable surrounding an impedance wire may be used. The retractable cables may be electrically connected to circuitry within the base 5 of the body fat scale.

In another exemplary embodiment, cables extend from the handheld body fat sensor 15 through retractable lever arms 22 or through the pedestal 17 and into the base 5 of the body fat scale. The cables may be electrically connected to circuitry within the base 5.

The monitor 10 may comprise an electronic LED or LCD display. In an exemplary embodiment the monitor 10 allows the user to program specific user profile information such as gender, age, and height. The body fat scale may be capable of storing several user profiles. The body fat scale circuitry may also be capable of compensating for variations in impedance due to such factors as hydration and motion.

In an exemplary embodiment, the user may program user information which appears in a single LCD located in the monitor 10. This single LCD may also display information to the user such as weight and percentage body fat. The user information may be programmed by touchpad entries.

In operation, an exemplary embodiment of the body fat scale allows the user to obtain both weight and body fat percentage measurements. The user may enter and store specific user profile information. The user may stand on the platform 7 of the base 5 to obtain an electronic weight reading which may be displayed by a single LED or LCD. The user may then choose to obtain a body fat reading. The user may make this selection by pressing a touch pad with the user's toe or foot. In one embodiment, the user then reaches down to grasp the handheld body fat sensor 15 connected to a pair of retractable cables 12.

The user then may activate a "start" button which may be located on the handheld body fat sensor 15. The handheld body fat sensor 15 sends a current throughout the upper body of the user. An electronic circuit for carrying out an impedance measurement may be located within the base 5 of the body fat scale. The electronic circuit within the base 5 then uses the impedance reading from the handheld body fat sensor 15 to calculate the user's percentage body fat. User profile information may be factored into the calculation. The user's body fat percentage may be displayed on an LCD. The LCD may alternately display weight and body fat percentage. Alternatively, the body fat reading may be displayed on a separate LCD so that the weight and body fat percentage may be shown simultaneously.

In an another exemplary embodiment, the user may grasp handheld body fat sensors 15 located at the end of retractable lever arms 22 connected to a pedestal 17. In another exemplary embodiment the user may grasp handheld body fat sensors 15 located at the end of retractable telescoping extensions 32. The body fat reading may then be obtained as described above.

Measurements performed in accordance with methods and body fat scales of the present invention correlate well with underwater body weighing methods demonstrating a high degree of accuracy.

While the above description contains specific examples, these should not be construed as limitations on the scope of the invention. Many other variations are possible within the teachings of the present invention and would be apparent to a person skilled in the art. Thus the scope of the invention should be determined by the appended claims and their legal equivalents, and not by the examples given.

What is claimed is:

1. A body fat scale comprising:
   a base having a bottom surface and a top surface;
   at least one retractable cable having a proximal end and a distal end; and
   at least one handheld body fat sensor connected to the distal end of the retractable cable.

2. The body fat scale of claim 1, wherein the proximal end of the retractable cable is connected to a retraction mechanism.

3. The body fat scale of claim 2, wherein the retraction mechanism is located within the base.

4. The body fat scale of claim 3, wherein the retraction mechanism is selected from the group consisting of a negator type spring assembly, a motorized spring assembly, and a counterbalance weight system.

5. The body fat scale of claim 3, wherein the proximal end of the retractable cable is connected to circuitry within the base.

6. The body fat scale of claim 3 further comprising a monitor.

7. The body fat scale of claim 6, wherein the monitor comprises a display.

8. The body fat scale of claim 7, wherein the display includes at least one of an LED and an LCD.

9. A body fat scale comprising:
- a base having a bottom surface and a top surface;
- a pedestal having a proximal end and a distal end, wherein the proximal end of the pedestal is connected to the base;
- at least one retractable lever arm having a proximal end and a distal end, wherein the retractable lever arm is pivotally connected directly to the pedestal near the distal end of the pedestal; and
- at least one handheld body fat sensor connected near the distal end of the retractable lever arm.

10. The body fat scale of claim 9, wherein a cable having a proximal end and a distal end extends through the retractable lever arm, wherein the distal end of the cable connects to the handheld body fat sensor and the proximal end of the cable connects to circuitry.

11. A body fat scale comprising:
- a base having a bottom surface and a top surface;
- at least one retractable telescoping extension having a proximal end and a distal end, wherein the proximal end of the retractable telescoping extension is connected to the base; and
- at least one handheld body fat sensor connected to the distal end of the retractable telescoping extension.

12. The body fat scale of claim 11, wherein a cable having a proximal end and a distal end extends through the retractable telescoping extension, wherein the distal end of the cable connects to the handheld body fat sensor and the proximal end of the cable connects to circuitry within the base.

13. The body fat scale of claim 12, wherein the retractable telescoping extension is conductive, and wherein the proximal end of the retractable telescoping extension is connected to circuitry within the base.

14. A method of measuring the body fat content of a person comprising:
- standing on a body fat scale platform;
- grasping a pair of handheld body fat sensors retractably connected to the body fat scale platform;
- transmitting a current through the sensors and the upper extremities of the person;
- measuring the impedance of the upper extremities of the person; and
- calculating the body fat percentage of the person based on the measured impedance.

* * * * *